Figure 1:
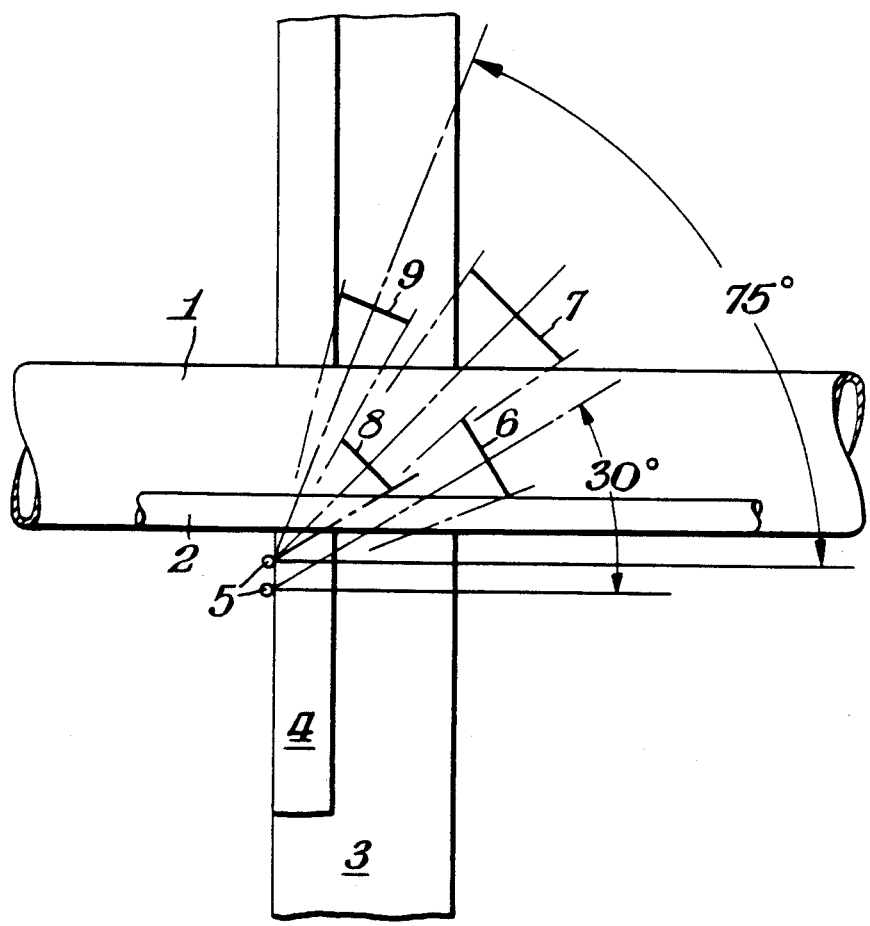

United States Patent [19]

Heiskel

[11] Patent Number: 4,974,246
[45] Date of Patent: Nov. 27, 1990

[54] PROCESS FOR CONTROLLING CORROSION OF PIPE

[75] Inventor: Georg Heiskel, Weilerswist, Fed. Rep. of Germany

[73] Assignee: DEA Mineralol Aktiengesellschaft, Wesseling, Fed. Rep. of Germany

[21] Appl. No.: 249,854

[22] Filed: Sep. 27, 1988

[51] Int. Cl.⁵ ............................................. G01B 15/02
[52] U.S. Cl. ..................................... 378/59; 378/58; 378/54
[58] Field of Search ..................... 378/57–60, 378/54, 55, 195–196; 250/306–308

[56] References Cited

U.S. PATENT DOCUMENTS 4,695,729 9/1987 Monno et al. .......................... 378/59

FOREIGN PATENT DOCUMENTS 3425197 5/1985 Fed. Rep. of Germany ........ 378/59

Primary Examiner—Carolyn E. Fields
Assistant Examiner—David P. Porta
Attorney, Agent, or Firm—Connolly and Hutz

[57] ABSTRACT

The invention relates to an improved process for controlling corrosion of pipe, which rests on supports or which is clamped by pipe-clamps, by the use of gamma ray and/or x-rays radiation.

17 Claims, 5 Drawing Sheets

PROCESS FOR CONTROLLING CORROSION OF PIPE

BACKGROUND OF THE INVENTION

It is known that pipe in technical plants is exposed to corrosive attack. This applies to pipe, which is in operation as well as to pipe out of operation. The condition of pipe material therefore has to be carefully controlled. Corrosive attack takes place in particular at positions on the external wall, where pipe rests on supports or where pipe is fixed by pipe-clamps. corrosive attack is also observed for example beneath coats of paints or at the internal wall of pipe in these areas. Corrosion can be detected by physical methods. By these methods it can be determined, whether only slight, medium or heavy corrosive destruction of pipe material has taken place. They also permit the determination of remaining wall thickness.

One of the methods, which are technically applied, is ultrasonic testing. By using this method, pipe which is to be investigated and which rests on supports, has to be lifted by at least 100 mm. It is also necessary to clean and polish respectively grind the parts to be tested.

Pipe corrosion can also be determined by application of gamma ray or x-rays radiation. If this method is applied in the support area, again pipe has be lifted by at least 50 mm.

In order to determine corrosion below pipe-clamps, pipe has to be supported provisionally and the pipe-clamp has to be opened.

Lifting of pipes usually is associated with considerable requirements. Pipes have to be taken out of operation and have to be purged, flanges have to be disconnected and dependent on the size of pipe, heavy lifting utilities have to be employed. In addition, units, which are connected to pipes to be tested, often have to be shut down. As a consequence, losses of production have to be accepted. An additional disadvantage in conventional testing procedures is the risk of breaking pipe at corroded positions during lifting. This may also quite easily happen, if pipe is lifted by forcing wedges between pipe and support.

Although corrosion testing of pipe is carried out in countless units, no testing procedure is available, which permits testing of pipe resting on supports or clamped by pipe-clamps, without being forced to lift the pipe above the support or to open the pipe-clamp or even to shut down the units connected to the pipe to be tested.

The instant invention provides an improved method to the artisan for controlling corrosion by using gamma-ray radiation or x-ray radiation at the support and clamp area without the disadvantages of the state of the art described above.

DESCRIPTION OF THE INVENTION

The invention relates to an improved process for the determination of corrosion of pipe, which rests on supports or which rests in pipe-clamps, of the support or pipe-clamp area by application of gamma ray or x-rays radiation and recording on radiographic film or recording by other radiation acceptors and radiation recording devices, characterized in that a, the source of gamma and/or x-ray radiation is positioned at one side of the pipe at one side of the support and a radiographic film is positioned at the other side of the pipe and the opposite side of the support, whereby the central connecting line between source of radiation and film forms an angle with the longitudinal axis of the pipe of 30° to 75°; the source of radiation is positioned in such a vertical position with regard to the support surface, that the lower edge of the source of radiation is positioned up to 0.5 D below and up to 1 D above the support surface, preferably up to 0.25 D below and up to 0.5 D above the support surface, whereby D is the diameter of the source of radiation; the film is positioned in such a way that adequate contrast is obtained on the film; the source of radiation and/or the film are positioned at a distance of not more than 100 cm, preferably less than 50 cm to the point of intersection of support surface and pipe; and preferably at least two exposures are made in such a way, that the first exposure is made as described above and that a second exposure is made in such a way that source of radiation and film are positioned at the same side of the pipe, however at the opposite side of the support or that the source of radiation and the film are positioned at the opposite side of the pipe and at the opposite side of the support: and in that b, the source of gamma ray and/or x-ray radiation is positioned at one side of the pipe at the side of the pipe-clamp and the radiographic film is positioned at the other side of the pipe at the opposite side of the pipe-clamp, whereby the central connecting line between source of radiation and film forms an angle with the longitudinal axis of the pipe of 30° to 75°, preferably of 50° to 70°; the source of radiation is positioned in such a vertical position to the pipe-clamp area to be investigated, that the center of the source of radiation is positioned up to 25 D below and up to 25 D above the internal surface of the pipe-clamp preferably up to 10 D below and up to 10 D above the internal surface of the pipe-clamp, whereby D is the diameter of the source of radiation; the film is positioned in such a way that adequate contrast is obtained on the film; source of radiation and/or film are positioned at a distance of not more than 100 cm, preferably less than 50 cm to the point of contact between pipe-clamp and pipe at the area to be tested; depending on the width of the pipe-clamp in case of larger width, preferably two exposures are made in such a way that the first exposure is made as described above and that a second exposure is made in such a way that source of radiation and film are positioned at the same side of the pipe, however at the opposite side of the pipe-clamp or that the source of radiation and film are positioned at the opposite side of the pipe and at the opposite side of the pipe-clamp.

By analogy the invention similarly applies, if pipe and support don't form an angle of 90°. Furthermore the instant invention relates to a device for the determination of corrosion of pipe, which rests on supports, or which rests in pipe-clamps, at the support or pipe-clamp area by application of gamma or x-ray radiation and recording on radiographic film or recording by other radiation acceptors and radiation recording devices, characterized in that a, the source of gamma and/or x-ray radiation is positioned at one side of the pipe at one side of the support and a radiographic film is positioned at the other side of the pipe and the opposite side of the support, whereby the central connecting line between source of radiation and film forms an angle with the longitudinal axis of the pipe of 30° to 75°; the source of radiation is positioned in such a vertical position with regard to the support surface, that the lower edge of the source of radiation is positioned up to 0.5 D below and up to 1 D above the support surface, preferably up to 0.25 D below and up to 0.5 D above the support surface, whereby D is the diameter of the source of radiation; the film is positioned in such a way that adequate contrast is obtained on the film; the source of radiation and/or the film are positioned at a distance of not more than 100 cm, preferably less than 50 cm to the point of intersection of support surface and pipe; and preferably in that for the preparation of preferably two exposures in the case of the first exposure, source of radiation and film are positioned as described above and in the case of the second exposure source of radiation and film are positioned at the same side of the pipe, however at the opposite side of the support or that the source of radiation and the film are positioned at the opposite side of the pipe and at the opposite side of the support and in that b, the source of gamma ray and/or x-ray radiation is positioned at one side of the pipe at the side of the pipe-clamp and the radiographic film is positioned at the other side of the pipe at the opposite side of the pipe-clamp, whereby the central connecting line between source of radiation and film forms an angle with the longitudinal axis of the pipe of 30° to 75°, preferably of 50° to 70°; the source of radiation is positioned in such a vertical position to the pipe-clamp area to be investigated, that the center of the source of radiation is positioned up to 25 D below the internal surface of the pipe-clamp and up to 25 D above the internal surface of the pipe-clamp, preferably up to 10 D below and to up to 10 D above the internal surface of the pipe-clamp, whereby D is the diameter of the source of radiation; the film is positioned in such a way that adequate contrast is obtained on the film; source of radiation and/or film are positioned at a distance of not more than 100 cm, preferably less than 50 cm to the point of contact between pipe-clamp and pipe at the area to be tested; in that depending on the width of the pipe-clamp in cases of pipe-clamps with a larger width for the preparation of preferably two exposures in the case of the first exposure, source of radiation and film are positioned as described above and in the case of the second exposure, source of radiation and film are positioned at the same side of the pipe, however at the opposite side of the pipe-clamp or that the source of radiation and the film are positioned at the opposite side of the pipe and at the same side of the pipe-clamp.

Pipe very often is located on piperacks or other support devices and rests at certain positions on the supports. According to the instant invention, support areas can be reliably tested at the internal and external walls with regard to corrosion, for example like pitting and abrasion.

Very often pipe is clamped by pipe-clamps. This may occur by suspended pipe-clamps or by fixing the pipe-clamp at the site of the pipe or below the pipe. The external surface of the pipe, which is located under the pipe-clamp can be tested according to the state of the art only in such a way that the pipe is provisionally supported or fixed in one way or another and that the pipe-clamp is opened subsequently. In such a case the instant invention again offers an essential improvement compared to the state of the art, in that it is possible to test the external and external surface of the pipe covered by the pipe-clamp by tangential as well as diagonal radiation in analogy to testing support areas, without the disadvantages of the state of the art described above.

The instant method of non-destructive testing uses gamma ray or x-ray radiation, which passes through the support and pipe-clamp areas and furnishes a picture on a radiographic film. In contrast to the state of the art the inventive process is not limited to empty pipe. Emptying, purification, polishing, removing of the insulation and in particular lifting of the pipe and disconnecting of the pipe to units in operation, which often causes shutdown of the unit are avoided by the inventive method. By analogy pipe-clamps have not be opened or to be removed.

FIGS. 1 to 6 show exemplary inventive devices.

As outlined above the use of gamma ray and x-ray radiation for corrosion testing is known. In the case of gamma ray radiation sources, generally small radioactive rods are used of a diameter of only a few millimeters. The radioactive material is usually iridium and cobalt. But also other radioactive materials may be used. The source of radiation itself generally is housed in a working and transportation container. During testing the radioactive source can be shifted for example with the aid of remote control out of the container through a hose or tube, whereby the source is brought into testing position.

The cased source of radiation is preferably brought into a stable position by an adjustable positioning device at the side of a support or of a pipe-clamp. At the opposite side a radiographic film is also brought into stable position by an adjustable positioning device in such a way that the radiation passing through the testing area furnishes an exposure, which leads to adequate contrasts on the film.

X-ray films may be used according to the invention. Preferably a film-amplifying foil combination is used with the result that the time of exposure is reduced compared to the time of exposure according to the state of the art, by at least 80%. This has the important effect that exposure of the human body to radiation is only short and reduced to a small area. However also other devices for accepting and recording of gamma ray and x-ray radiation may be applied, for example devices which work according to the Geiger counter principle. The essential inventive characteristic however is that the radiation passes tangentially as well as diagonally through the area to be tested at the conditions outlined in claim 1 and 11.

Intensity and wave length of the source of radiation for testing of corrosion at pipes are known to the artisan and have not to be elucidated further.

The sources of radiation used in the instant invention may have different activities of radiation. This is also known to the artisan. Gamma ray radiation of variable activities is preferred.

According to the inventive process the source of radiation, which, as described above, is usually located in a casing, is brought into testing position close to the support or pipe-clamp by a positioning device in such a way that in the case of supports the central connecting line between source of radiation and film from an angle of 30° to 75° with the longitudinal axis of the pipe, respectively in the case of pipe-clamps form an angle of 30° to 75°, preferably of 50° to 70° between central connecting line between source of radiation and film and longitudinal axis of the pipe.

As a result of the investigations of applicant, the source of radiation has to be positioned, in order to obtain pictures with sufficient contrast, with the lower edge up to 0.5 D below the support surface and up to 1 D above the support surface. Preferably the source of radiation is positioned up to 0.25 D below and up to 0.5 D above the support surface, whereby it may be positioned centrally at the height of the support point.

If for example the source of radiation has a diameter of 1.6 mm, the lower edge of the source may be positioned up to 0.8 mm, preferably up to 0.4 mm below the surface of support. On the other hand the lower edge may be positioned up to 1.6 mm above the support surface, preferably up to 0.8 mm.

By analogy in the case of testing areas covered by pipe-clamps, the source of radiation has to be in such a position that the center of the source of radiation is up to 25 D below the connecting line pipe wall / pipe-clamp at the site of testing and up to 25 D above the connecting line, preferably up to 10 D below to up to 10 D above this line, whereby D is the diameter of the source of radiation.

The source of radiation may be preferable positioned centrally to this line and close to the support.

In the case of pipe-clamps the covered pipe area can be tested according to the invention around the whole pipe. The distance between source of radiation and film to the point of intersection of support surface and pipe respectively to the point of contact between pipe and pipe-clamp at the site to be tested, may be up to 100 cm, preferably below 50 mm, whereby distances as short as possible are preferred. Source of radiation and film thus may be located at the height outlined above in a segment with a radius of 100 cm or less.

The film is positioned in such a way that an adequate contrast is obtained after exposure in order to reliable detect corrosion.

Preferably two exposures are made. In principle even more exposures can be made. It has to be taken into consideration that often one exposure from one direction does not furnish a result, which can be reliably evaluated, except in those cases, where the surface of support is sufficiently small, respectively the support device is sufficiently narrow.

By analogy in cases of pipe-clamps one exposure is only sufficient, if the pipe-clamp is sufficiently narrow.

In the case of making two exposures, one proceeds according to the invention preferably in such a way that in the case of the second exposure source of radiation and film are positioned at the opposite site of the support respectively of the pipe-clamp, however at the same site of the pipe or at the opposite site of the pipe and at the opposite side of support respectively pipe-clamp.

A particularly advantageous effect of the inventive process results from the fact, that pipes have not to be lifted above the support surface. The pipe has not to be purged, flanches have not to be opened nor blind covers have to be set. In particular testing has no effect on operation of units, which are connected to the pipes to be tested. By analogy testing in the area under pipe claims can be carried out without an preparation of the site.

In a particular example corrosion testing is applied to an ethylene production unit with a capacity of 200.000 t/a. Corrosion testing in such a unit according to the state of the art may cause up to 10 days of additional shut-down during a usual period of revision. Application of the inventive process, which can be carried out independent of the revision saves loss of production of 6.000 t of ethylene or approximately of 6 million German marks. This case is only to be considered as an example, since according to the invention pipe can be tested in any unit. However this example clearly shows the importance of the inventive process.

The investigations of applicant have led to the result that pipes of an internal diameter of 30 mm to 300 mm, preferably of 50 mm to 250 mm can be tested very reliably.

The thickness of the pipe wall is in the case of testing of external corrosion at areas of support or pipe-clamps without significance, since the extent of corrosion can be calculated, based on the pictures taken. In cases where corrosion is determined by other methods, for example by direct evaluation of pictures with the aid of a slide caliper, the contour of the internal pipe wall has to be identifiable.

In such a case the wall thickness should not exceed 20 mm, whereby the lower limitation of the wall thickness usually is 1 mm. Preferably the wall thickness should be 1 to 12 mm.

The same wall thickness applies to testing of internal corrosion. Considering exemplarily pipe-clamps of a width of 30–60 mm and a thickness of the pipe-clamp of 5 to 10 mm, the pipe wall thickness should also be preferably 1 to 12 mm.

It is known to the artisan that the quality of pictures obtained by using gamma ray radiation also depends on the media flowing through the pipe. To a certain extent and comparable to the state of the art, this effect also applies to testing according to the instant invention.

The pipe materials may be any material in particular however materials based on steel as well as stainless steel, but also other materials and alloys.

According to the invention insulation of pipes has not to be removed for testing. Furthermore cleaning, grinding, polishing, removing of paint and so on, is not necessary. Not only the area of support and pipe-clamp itself but also the close vicinity can be tested. Based on the exposed radiographic film the remaining wall thickness can be reliably calculated, by relating the distances between source of radiation and center of the pipe and the distance between source of radiation and film to the actual wall thickness and wall thickness shown on the picture.

Abrasion, pitting and other types of corrosion thus can be reliably determined.

FIGURES AND EXAMPLES

The invention is further explained by the following figures:

FIG. 1

In FIG. 1 a pipe with an internal diameter of 250 mm is represented
by (1).
(2) represents a 50 mm pipe.
(3) is a relatively broad, (4) a narrow site of support. Sources
of radiation are represented by (5). (6)–(9) are radiographic films.

The angles shown are formed by the longitudinal axis of the
pipes and the central connecting line between source at the pipe segments in question after the segments have been removed from the supports (right column).

The results show that the inventive method gives excellent results.

Comparison of remaining wall thickness obtained at pipes resting on supports by the new URBK-method with data obtained by mechanical measurements directly at the open pipe segments.

| Sample Nr. | Nominal size of pipe (inner diameter) mm | Wall thickness mm | Width of support mm | Corrosion measurements by URBK-method | | | Remaining wall thickness calculated by URBK-method mm | Remaining wall thickness by direct measurement at the open pipe-segment mm |
|---|---|---|---|---|---|---|---|---|
| | | | | external wall at the support area | rust formation below the paint coat | internal wall at the support area | | |
| 5 | 250 | 6,0 | 70 | medium strong | — | — | 4,2 | 4,3 |
| 14 | 100 | 4,0 | 160 | strong | — | — | 2,1 | 2,2 |
| 35 | 100 | 4,0 | 160 | medium | — | — | 2,7 | 2,7 |
| 52 | 100 | 4,0 | 160 | very strong close to breaking | yes | — | 0,8 | 0,8 |
| 82 | 80 | 4,0 | 220 | strong | yes | — | 2,1 | 2,0 |
| 59 | 150 | 5,5 | 220 width of pipe-clamp | — external surface of pipe in the pipe-clamp area | — | strong | 3,7 | 3,5 |
| 62 | 250 | 10,0 | 50 | medium-strong | — | — | 4,5 | 4,5 | of radiation
and center of the radiographic film.

FIG. 2

Figure 2:
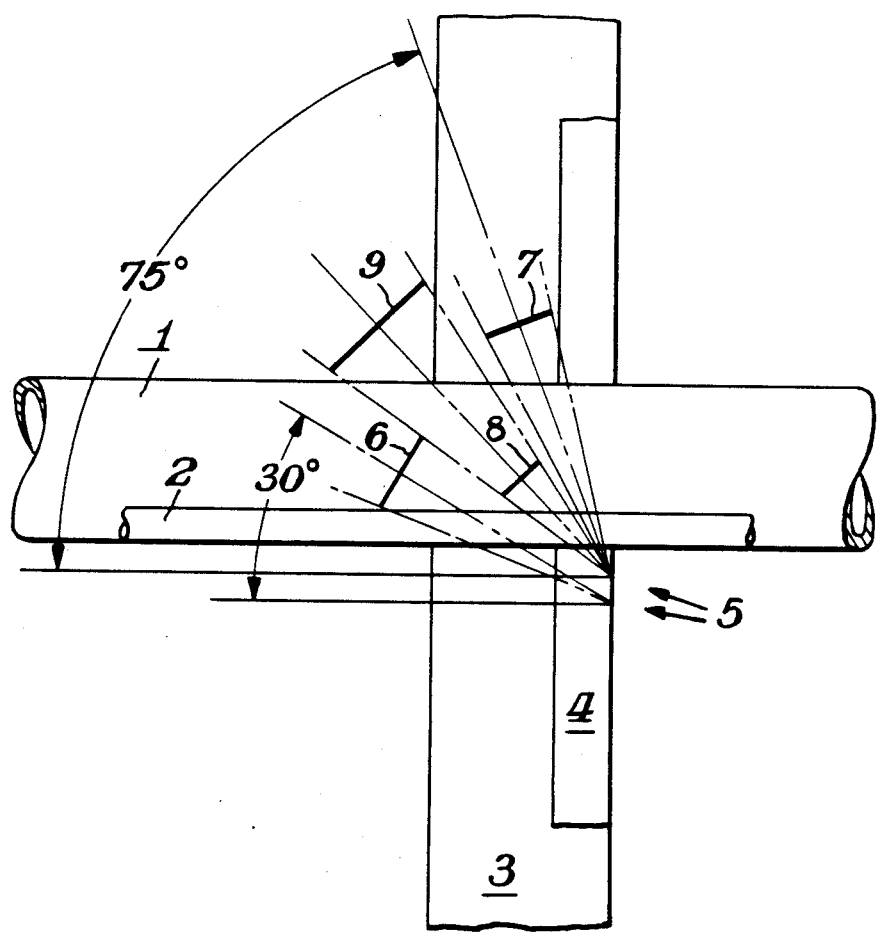

In FIG. 2 a second exposure is represented, whereby source of radiation and film are arranged at the opposite side of the support.

FIG. 3

Figure 3:
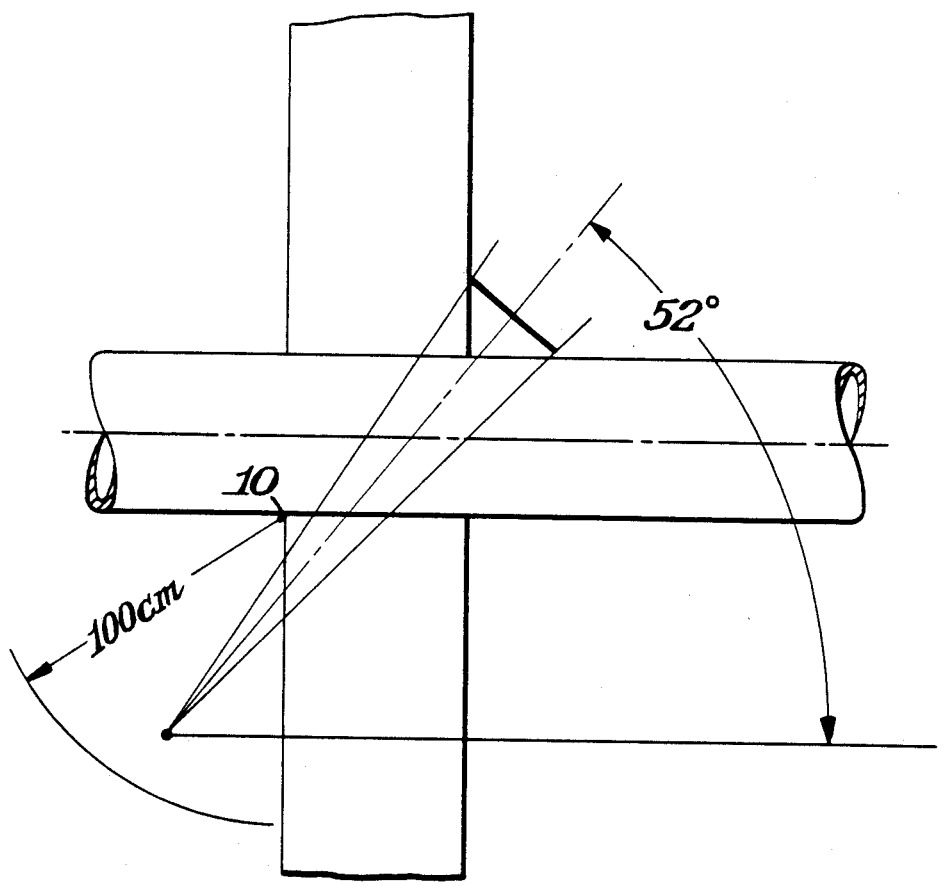

In FIG. 3 the position of the source of radiation is located in a segment formed within a distance of 100 cm to the point of intersection of support surface and pipe.

Figure 4:
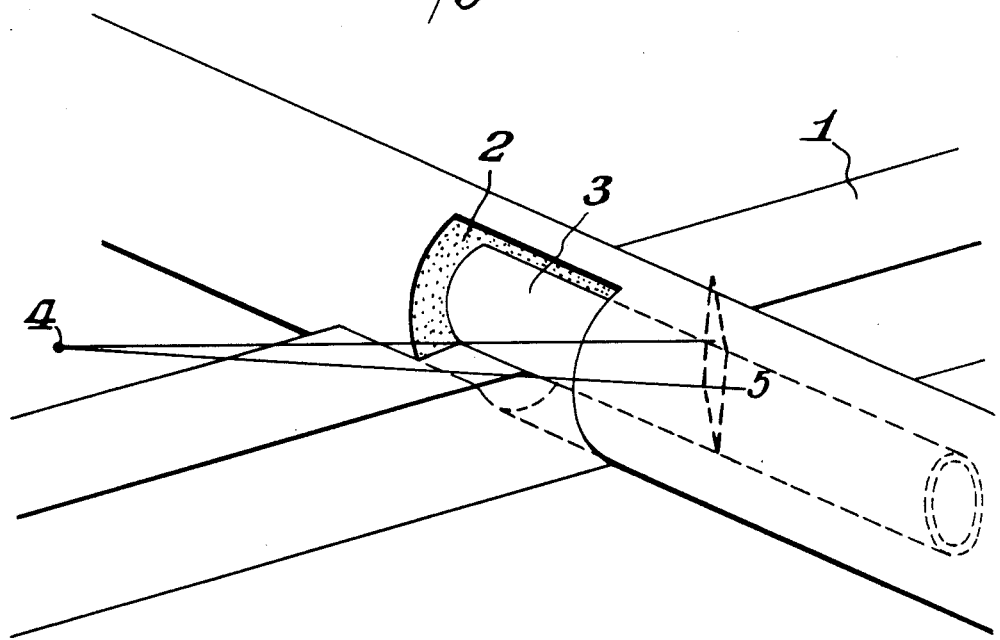
Figure 5:
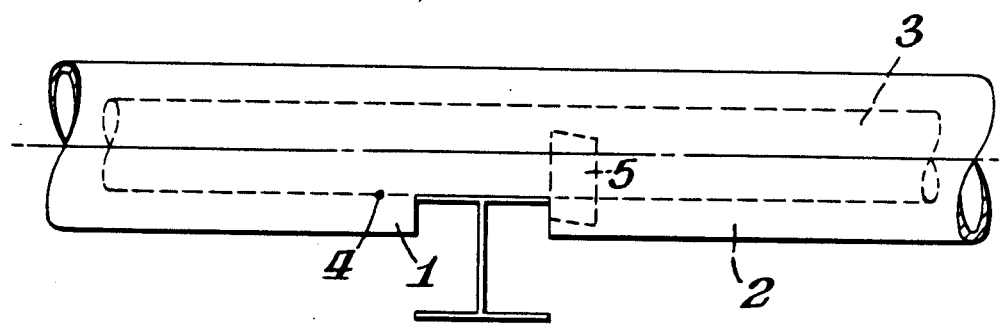

FIGS. 4 and 5

In FIGS. 4 and 5 insulated pipes are shown. The pipes rest
on supports. At these positions segments are cut out of the
insulation.
(1) represents in both figures the support, (2) the insulation,
(3) the pipe, (4) the source of radiation and (5) the film respectively other recording devices positioned behind the
insulated pipe.

FIG. 6

Figure 6:
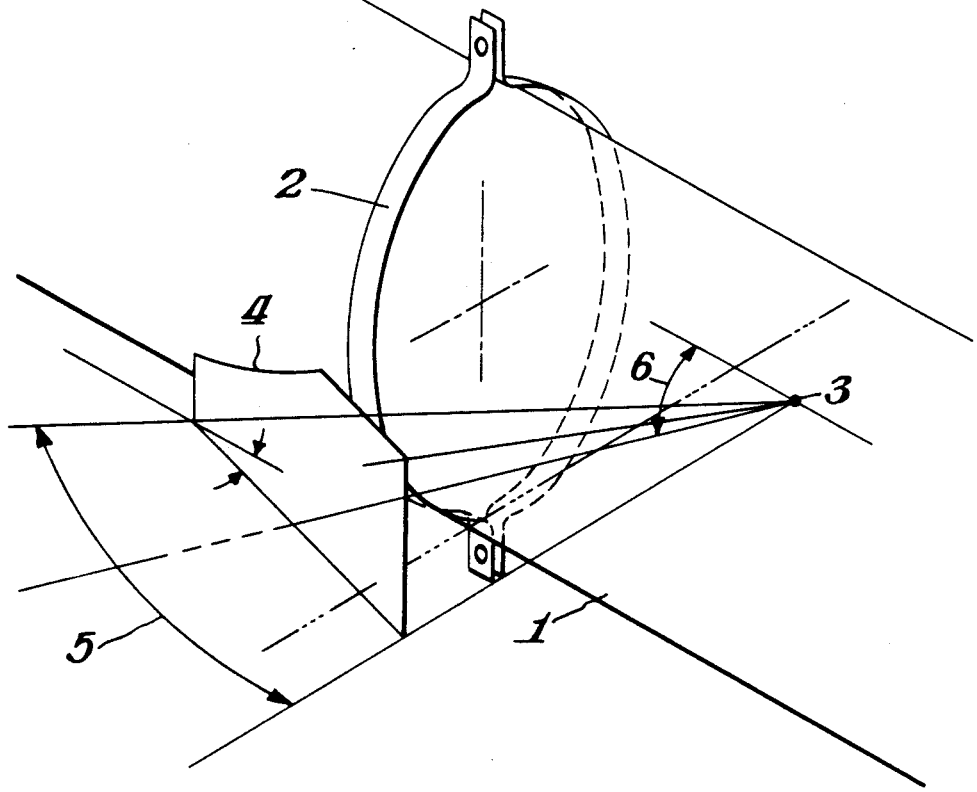

In FIG. 6 a typical set up for corrosion testing under a pipe-clamp is shown. (1) represents the pipe in the testing area, (2) the pipe-clamp, (3) the source of radiation and (4) the radiographic film. (5) is the angle of the central gamma ray beam in the plane of the longitudinal axis of the pipe. (6) represents the angle between the central gamma ray directed to the center of the film and the longitudinal axis of the pipe.

The table shows remaining wall thickness of various pipes, determined by the inventive method (second column from right to left) compared to remaining wall thickness obtained by direct mechanical measurement

I claim:

1. Improved process forth determination of corrosion of pipe, which rests on supports or which rests in pipe-clamps, at the support or pipe-clamp area by application of gamma ray or x-ray radiation or both and recording on a radiographic acceptor characterized in that he source of radiation is positioned atone side of the pipe and at one side of the support or pipe-clamp and a radiographic acceptor is positioned at the other side of the pipe and the opposite side of the support or pipe-clamp, whereby the central connecting line between the source of radiation and the acceptor forms an angle with the longitudinal axis of the pipe of 30° to 75° and the source of radiation is positioned in such a vertical position with regard to the support surface, that
  (a) when the pipe rests on supports, the lower edge of the source of radiation is positioned up to 0.5 D below and up to 1 D above the support surface or
  (b) when the pipe rests in pipe clamps, the center of the source of radiation is positioned up to 25 D below the internal surface of the pipe-clamp and to up to 25 D above the internal surface of the pipe-clamp,
whereby D is the diameter of the source of radiation and the acceptor is positioned in such a way that adequate contrast is obtained on said acceptor and the source of radiation, the acceptor or both are positioned at a distance of not more than 100 cm to the point of intersection of support or pipe-clamp surface and pipe.

2. Process according to claim 1, characterized in that a gamma ray radiation source is used.

3. Process according to claim 1 characterized in that at the side of exit of the gamma ray or x-ray radiation a combination of radiographic film - amplifying foil is used.

4. Process according to claim 1 characterized in that pipe is tested with an internal diameter of 30 to 300 mm.

5. Process according to claim 1 characterized in that pipe is tested with an internal diameter of 50 to 250 mm.

6. A process according to claim 1 wherein a fist exposure is made as described in claim 1 and at least one additional exposure is made in such a way that, in the second exposure, the source of radiation and acceptor remain on their respective sides of the pipe but exchange positions relative to the sides of the support or pipe-clamp.

7. A process according to claim 1 wherein the central connecting line between source of radiation and support or pipe-clamp forms an angle with the longitudinal axis of the pipe of 50° to 75°.

8. A process according to claim 1 wherein the pipe rests on pipe-lamps and the source of radiation is positioned in such a vertical position to the pipe-clamp area to be investigated that the center of the source of radiation is positioned up to 10 D below the internal surface of the pipe-clamp and to 10 D above the internal surface of the pipe-clamp.

9. Process according to claim 1 characterized in that the remaining wall thickness of the pipe is calculated on the basis of film-exposures made.

10. Process according to claim 1 characterized in that the support area is tested where the pipe rests within the pipe-clamp.

11. A process according to claim 1 wherein the pipe rests on supports and the lower edge of the source of radiation is positioned up to 0.25 D below and up to 0.5 D above the support surface.

12. Device for the determination of corrosion of pie, which rests on supports or which rests in pipe-clamps at the support or pipe-clamp area by application of gamma ray or x-ray radiation or both and recording on a radiographic acceptor characterized in that the source of radiation is positioned at one side of the pipe ad at one side of the support or pipe-clamp and a radiographic acceptor is positioned at the other side of the pipe and the opposite side of the support or pipe-clamp, whereby the central connecting line between the source of radiation and the acceptor forms an angle with the longitudinal axis of the pipe of 30° to 75° and the source of radiation is positioned in such a vertical position with regard to the support surface, that
  (a) when the pipe rests on supports, the lower edge of the source of radiation is positioned up to 0.5 D below and up to 1 D above the support surface or
  (b) when the pipe rests in pipe-clamps, the center of the source of radiation is positioned up to 25 D below the internal surface of the pipe-clamp and to up to 25 D above the internal surface of the pipe-clamp, whereby D is the diameter of the source of radiation and the acceptor is positioned in such a way that adequate contrast is obtained on said acceptor and the source of radiation, the acceptor or both are positioned at a distance of not more than 100 cm to the point of intersection of support or pipe clamp surface and pipe.

13. Device according to claim 12, characterized in that at the side of exit of the gamma ray or x-ray radiation a combination of radiographic film amplifying foil is positioned.

14. Device according to claim 12 characterized in that the source of radiation is positioned by an adjustable positioning-device.

15. Device according to claim 12 characterized in that the source of radiation is positioned adjacent to the side of the support.

16. Device according to claim 12, characterized in that the source of radiation is a gamma ray radiation source.

17. Device according to claim 12, characterized in that the radiographic acceptor is positioned by an adjustable positioning-device.

* * * * *